United States Patent [19]

Engelhardt et al.

[11] 4,214,001
[45] Jul. 22, 1980

[54] 1-(4-ACYLAMINO-PHENYL)-2-AMINO-ETHANOLS AND SALTS THEREOF

[75] Inventors: Günther Engelhardt; Johannes Keck; Krüger, all of Biberach an der Riss; Klaus Noll, Warthausen; Helmut Pieper, Biberach an der Riss, all of Fed. Rep. of Germany

[73] Assignee: Boehringer Ingelheim GmbH, Ingelheim am Rhein, Fed. Rep. of Germany

[21] Appl. No.: 883,814

[22] Filed: Mar. 6, 1978

[30] Foreign Application Priority Data

Mar. 14, 1977 [DE] Fed. Rep. of Germany ....... 2710997

[51] Int. Cl.² .................. A61K 31/27; A61K 31/275; C07C 121/80; C07C 125/06
[52] U.S. Cl. ................. 424/300; 260/465 D; 260/553 A; 424/304; 424/322; 560/22; 560/27; 560/29; 560/30
[58] Field of Search ......... 560/21; 260/465 D, 553 A; 560/29; 424/304, 300, 322

[56] References Cited

U.S. PATENT DOCUMENTS 4,063,025 12/1977 Murakami et al. ............... 560/29

*Primary Examiner*—Dolph H. Torrence
*Attorney, Agent, or Firm*—Hammond & Littell, Weissenberger & Muserlian

[57] ABSTRACT

Compounds of the formula

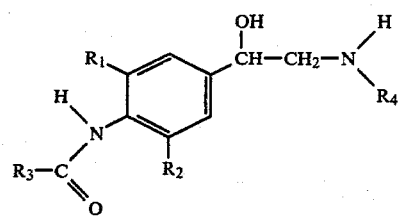

wherein
$R_1$ is hydrogen, halogen or cyano;
$R_2$ is fluorine, cyano, trifluoromethyl, nitro or alkyl of 1 to 4 carbon atoms;
$R_3$ is alkoxy of 1 to 5 carbon atoms, alkenyloxy of 2 to 5 carbon atoms, aryloxy of 6 to 10 carbon atoms, aralkoxy of 7 to 11 carbon atoms, or —$NR_5R_6$, where $R_5$ and $R_6$ are each hydrogen, alkyl of 1 to 5 carbon atoms, alkenyl of 2 to 5 carbon atoms, aryl of 6 to 10 carbon atoms or aralkyl of 7 to 11 carbon atoms; and
$R_4$ is cycloalkyl of 3 to 5 carbon atoms or alkyl of 3 to 5 carbon atoms;

and non-toxic, pharmacologically acceptable acid addition salt thereof. The compounds as well as the salts are useful as analgesics, uterospasmolytics and antiasthmatics.

12 Claims, No Drawings

1-(4-ACYLAMINO-PHENYL)-2-AMINO-ETHANOLS AND SALTS THEREOF

This invention relates to novel 1-(4′-acylamino-phenyl)-2-amino-ethanols and non-toxic acid addition salts thereof, as well as to methods of preparing these compounds.

More particularly, the present invention relates to a novel class of compounds represented by the formula

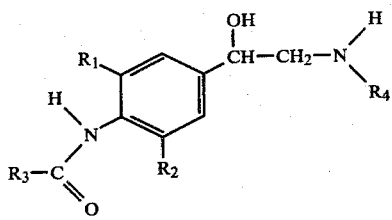

wherein
$R_1$ is hydrogen, halogen, or cyano;
$R_2$ is fluorine, cyano, trifluoromethyl, nitro or alkyl or 1 to 4 carbon atoms;
$R_3$ is alkoxy of 1 to 5 carbon atoms, alkenyloxy of 2 to 5 carbon atoms, aryloxy of 6 to 10 carbon atoms, aralkoxy of 7 to 11 carbon atoms, or —$NR_5R_6$, where $R_5$ and $R_6$ are each hydrogen, alkyl of 1 to 5 carbon atoms, alkenyl of 2 to 5 carbon atoms, aryl of 6 to 10 carbon atoms or aralkyl of 7 to 11 carbon atoms; and
$R_4$ is cycloalkyl of 3 to 5 carbon atoms or alkyl of 3 to 5 carbon atoms;
and non-toxic, pharmacologically acceptable acid addition salts thereof.

Examples of specific embodiments of substituents $R_1$ to $R_4$ in formula I are the following:
$R_1$—Hydrogen, fluorine, chlorine, bromine, iodine or cyano;
$R_2$—Fluorine, cyano, trifluoromethyl, nitro, methyl, ethyl, n-propyl, isopropyl, n-butyl, sec. butyl, isobutyl or tert. butyl;
$R_3$—Methoxy, ethoxy, n-propoxy, isopropoxy, n-butoxy, sec. butoxy, isobutoxy, tert. butoxy, n-pentyloxy, isopentyloxy, tert. pentyloxy, phenoxy, naphthyloxy, benzyloxy, phenylethoxy, allyloxy, butenyloxy, pentenyloxy, amino, methylamino, ethylamino, n-propylamino, isopropylamino, n-butylamino, sec. butylamino, isobutylamino, tert. butylamino, n-pentylamino, dimethylamino, diethylamino, di-n-propylamino, diisopropylamino, di-n-butylamino, di-sec. butylamino, diisobutylamino, di-tert. butylamino, di-n-petylamino, phenylamino, naphthylamino, benzylamino, phenylethylamino, methylethylamino, methylbenzylamino, methyl-n-propylamino, methyl-isopropylamino, methyl-n-butylamino, ethylpropylamino, ethyl-isopropylamino, diphenylamino, methyl-phenylamino, ethyl-phenylamino, isopropyl-phenylamino, allylamino, diallylamino, n-butenylamino or n-pentenylamino;
$R_4$—Isopropyl, sec. butyl, isobutyl, tert. butyl, cyclopropyl, cyclobutyl or cyclopentyl.

A preferred sub-genus is constituted by compounds of the formula I
wherein
$R_1$ is hydrogen, halogen or cyano;
$R_2$ is fluorine, cyano, trifluoromethyl, nitro or alkyl of 1 to 4 carbon atoms;
$R_3$ is alkoxy of 1 to 5 carbon atoms, alkenyloxy of 2 to 5 carbon atoms, aralkoxy of 7 to 11 carbon atoms or, when $R_1$ is hydrogen or halogen and $R_2$ is fluorine, trifluoromethyl or nitro, also —$NHR_6$, where $R_6$ is hydrogen, alkyl of 1 to 5 carbon atoms, alkenyl of 2 to 5 carbon atoms, aryl of 6 to 10 carbon atoms or aralkyl of 7 to 11 carbon atoms; and
$R_4$ is cycloalkyl of 3 to 5 carbon atoms or alkyl of 3 to 5 carbon atoms;
and non-toxic, pharmacologically acceptable acid addition salts thereof.

A further, especially preferred sub-genus is constituted by compounds of the formula I
wherein
$R_1$ is hydrogen, halogen or cyano;
$R_2$ is fluorine, cyano, trifluoromethyl, nitro or alkyl of 1 to 4 carbon atoms;
$R_3$ is alkoxy of 1 to 4 carbon atoms or, when $R_1$ is hydrogen or halogen and $R_2$ is fluorine, trifluoromethyl or nitro, also —$NHR_6$ where $R_6$ is hydrogen or alkyl of 1 to 4 carbon atoms; and
$R_4$ is isopropyl or tert. butyl;
and non-toxic, pharmacologically acceptable acid addition salts thereof.

The compounds embraced by formula I may be prepared by the following methods:

Method A

By reducing an acetophenone of the formula

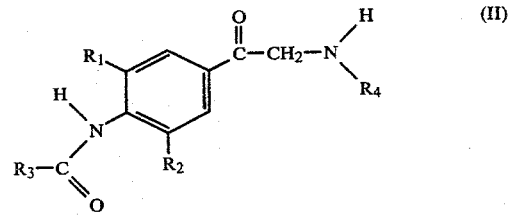

wherein $R_1$, $R_2$, $R_3$ and $R_4$ have the same meanings as in formula I.

The reduction is carried out in a suitable solvent, such as methanol, methanol/water, ethanol, isopropanol, butanol, diethylether, tetrahydrofuran or dioxane with a complex metal hydride, with aluminum isopropylate in the presence of a primary or secondary alcohol, with catalytically activated hydrogen or with nascent hydrogen, at temperatures between −20° C. and the boiling point of the solvent which is used.

Preferably, the reduction with a complex metal hydride is carried out with sodium borohydride or lithium aluminum hydride in a suitable solvent, such as methanol, methanol/water, diethyl ether or tetrahydrofuran, at temperatures between −20° C. and 50° C.; the reduction with aluminum isopropylate is effected at the boiling point of isopropanol while removing the formed acetone by distillation; the reduction with catalytically activated hydrogen is carried out with hydrogen in the presence of a catalyst, such as platinum, palladium, Raney nickel or Raney cobalt, at room temperature and at a hydrogen pressure of 1–5 atmospheres; and the reduction with nascent hydrogen, generated for instance by activated metallic aluminum and water or with zinc and hydrochloric acid, is carried out a temperature up to the boiling point of the solvent which is used.

Method B

By reducing an aldehyde of the formula

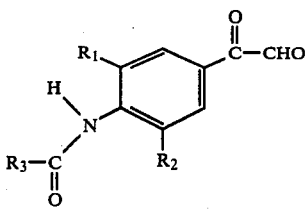

wherein $R_1$, $R_2$ and $R_3$ have the same meanings as in formula I, or a hydrate thereof, in the presence of a primary amine of the formula $$H_2N-R_4 \qquad (IV)$$

wherein $R_4$ has the same meanings as in formula I.

The reduction is carried out in a solvent, such as methanol, ethanol, butanol, diethyl ether, tetrahydrofuran or dioxane with a complex metal hydride or with catalytically activated hydrogen at temperatures between $-20°$ C. and the boiling point of the solvent which is used.

The reduction with a complex metal hydride, for example, with sodium borohydride or lithium aluminum hydride is performed in a suitable solvent such as methanol, methanol/water, diethyl ether or tetrahydrofuran, at temperatures, between $-20°$ C. and the boiling point of the solvent, for instance at temperatures between 0° and 50° C., and the reduction with catalytically activated hydrogen is carried out with hydrogen in the presence of a catalyst such as platinum, palladium, Raney nickel or Raney cobalt at temperatures between 0° and 100° C., but preferably at room temperatures, and at a hydrogen pressure of 1-5 atmospheres.

The reaction is advantageously performed in a manner such that the intermediate of the formula

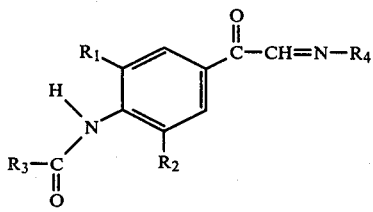

wherein $R_1-R_4$ have the meanings previously defined, which is formed in situ, is not isolated. However, if desired, the intermediate may also be isolated and then reduced in the manner described above.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, fumaric acid, 8-chlorotheophylline or the like.

The starting compounds of the formulas II and III can be prepared according to methods known from the literature. For example, a compound of the formula II is obtained by reacting a corresponding 2-halo-acetophenone with a corresponding amine; a compound of the formula III is obtained by oxidation of a corresponding acetophenone with selenium dioxide (see examples). It is not necessary to isolate the starting compound from the reaction mixtures.

The following examples illustrate the present invention and will enable others skilled in the art to understand it more completely. It should be understood, however, that the invention is not limited solely to the particular examples given below.

EXAMPLE 1

1-(4'-Ethoxycarbonylamino-3'-chloro-5'-fluorophenyl)-2-tert. butylamino-ethanol and its hydrochloride by method A 8.7 gm of 4'-ethoxycarbonylamino-3'-chloro-5'-fluoro-acetophenone were added in portions to a solution of 3.7 gm of selenium dioxide in 30 ml of dioxane and 1 ml of water at 60° C., while stirring, and the resulting mixture was refluxed for 4 hours. After cooling, 4.1 ml of tert. butylamine were added dropwise to the obtained solution of 4'-ethoxycarbonylamino-3'-chloro-5'-fluoro-phenylglyoxal on an ice bath. After completion of the addition, the mixture was diluted with 350 ml of ethanol, and the insoluble matter was filtered off. 5 gm of sodium borohydride were added in portions to the filtrate containing raw 4'-ethoxycarbonylamino-3'-chloro-5'-fluoro-phenyl-glyoxylidene-tert. butylamine, while stirring and cooling with ice. After standing overnight at room temperature, the excess sodium borohydride was destroyed with acetone, water was added, and the mixture was extracted with chloroform. The chloroform extract was then washed with water, dried with sodium sulfate, after the addition of activated charcoal briefly heated to boiling and, after filtering, evaporated to dryness in vacuo. The solid residue consisting of 1-(4'-ethoxycarbonylamino-3'-chloro-5'-fluoro-phenyl)-2-tert. butylamino-ethanol was then taken up in isopropanol, and the solution was acidified with ethereal hydrochloric acid to pH 4. After addition of ether the precipitated crystals were collected by suction filtration and washed with ether, yielding the hydrochloride of the formula

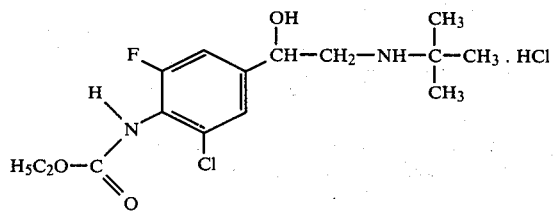

which had a melting point of 192°-193° C.

In analogous manner, the following compounds were also prepared:
 (a) 1-(4'-Ethoxycarbonylamino-3'-chloro-5'-trifluoromethylphenyl)-2-tert. butylamino-ethanol, M.p.: 168°-170° C. (decomposition).
 (b) 1-(4'-Ethoxycarbonylamino-3'-bromo-5'-fluorophenyl)-2-isopropylamino-ethanol hydrochloride, M.p.: 180°-182° C.
 (c) 1-(4'-Ethoxycarbonylamino-3'-bromo-5'-fluorophenyl)-2-tert.-butylamino-ethanol hydrochloride, M.p.: 197°-198° C. (decomposition)

(d) 1-(4'-Ethoxycarbonylamino-3'-fluoro-phenyl)-2-tert. butylamino-ethanol hydrochloride, M.p.: 235°–236° C.

(e) 1-(4'-Ethoxycarbonylamino-3'-cyano-5'-fluoro-phenyl)-2-tert.-butylamino-ethanol hydrochloride, M.p.: 198°–200° C. (decomposition)

(f) 1-(4'-Ethoxycarbonylamino-3'-nitro-phenyl)-2-tert. butylamino-ethanol hydrochloride, M.p.: 189°–190° C. (decomposition)

(g) 1-(4'-Ethoxycarbonylamino-3'-fluoro-5'-iodo-phenyl)-2-cyclopropylamino-ethanol, M.p.: 127°–130° C.

(h) 1-[3'-Fluoro-5'-iodo-4'-(3-methyl-ureido)-phenyl]-2-tert. butylamino-ethanol hydrochloride, M.p.: sintering from 115° C. (amorphous substance) Mass-spectrum ($C_{14}H_{17}N_3O_2FI$) Molpeak of the base: Found: 409 Calc.: 409.25

(i) 1-[3'-Fluoro-5'-iodo-4'-(3-methyl-ureido)-phenyl]-2-cyclopropyl-amino-ethanol hydrochloride, M.p.: 167°–170° C.

(j) 1-(3'-Cyano-5'-fluoro-4'-isobutyloxycarbonylaminophenyl)-2-tert.-butylamino-ethanol hydrochloride (The excess sodium borohydride was destroyed with dilute hydrochloric acid), M.p.: 189°–191° C.

(k) 1-(4'-Benzyloxycarbonylamino-3'-fluoro-5'-iodophenyl)-2-cyclopropylamino-ethanol (The excess sodium borohydride was destroyed with dilute hydrochloric acid), M.p.: 135°–137° C.

(l) 1-(4'-Allyloxycarbonylamino-3'-fluoro-5'-iodophenyl)-2-cyclopropylamino-ethanol (The excess sodium borohydride was destroyed with dilute hydrochloric acid), M.p.: 122°–123° C.

(m) 1-(3'-Fluoro-4'-isobutyloxycarbonylamino-5'-iodophenyl)-2-cyclopropylamino-ethanol (The excess sodium borohydride was destroyed with dilute hydrochloric acid), M.p.: 126°–128° C.

(n) 1-(4'-Ethoxycarbonylamino-3'-cyano-phenyl)-2-isopropylamino-ethanol, M.p.: 112°–115° C.

(o) 1-(4'-Ethoxycarbonylamino-3'-cyano-phenyl)-2-tert. butylamino-ethanol, M.p.: 78°–82° C.

EXAMPLE 2

1-(4'-Ethoxycarbonylamino-5'-bromo-3'-methyl-phenyl)-2-tert. butylamino-ethanol and its hydrochloride by method B 6.5 gm of bromine were added dropwise to a boiling solution of 12 gm of 4'-ethoxycarbonylamino-5'-bromo-3'-methylacetophenone in 200 ml of chloroform. The bromine was rapidly consumed while hydrobromic acid was evolved. The 4'-ethoxycarbonylamino-5', 2-dibromo-3'-methyl-acetophenone contained in the resulting solution was then converted into 4'-ethoxycarbonylamino-5'-bromo-3'-methyl-2-tert. butylaminoacetophenone by adding 14.6 gm of tert. butylamine and boiling the mixture for 30 minutes. The resulting solution was then evaporated to dryness in vacuo, the residue was taken up in a mixture of 50 ml of methanol and 20 ml of water, and the keto group was reduced by adding a solution of 3.8 gm of sodium borohydride in 20 ml of water while at the same time maintaining the pH of the reaction mixture between 6 and 8 by addition of hydrochloric acid. After completion of the reduction, the methanol was distilled off, the residue was diluted with water, the aqueous mixture was made distinctly alkaline with ammonia, and the alkaline solution was extracted with chloroform. The organic extract solution was evaporated to dryness, the residue was purified on a silica-gel column (eluant: chloroform-/methanol 2:1), the eluate was evaporated, the residue (the free base) was dissolved in ethanol, and the solution was acidified with ethereal hydrochloric acid, yielding 1-(4'-ethoxycarbonylamino-5'-bromo-3'-methyl-phenyl)-2-tert. butylamino-ethanol hydrochloride. M.p.: 212°–214° C. (decomposition).

In analogous manner the following compounds were also prepared:

(a) 1-(4'-Ethoxycarbonylamino-3'-chloro-5'-trifluoromethylphenyl)-2-tert. butylamino-ethanol, M.p.: 168°–170° C. (decomp.)

(b) 1-(4'-Ethoxycarbonylamino-3'-bromo-5'-fluoro-phenyl)-2-isopropylamino-ethanol hydrochloride, M.p.: 180°–182° C.

(c) 1-(4'-Ethoxycarbonylamino-3'-bromo-5'-fluoro-phenyl)-2-tert. butylamino-ethanol hydrochloride, M.p.: 197°–198° C. (decomp.)

(d) 1-(4'-Ethoxycarbonylamino-3'-fluoro-phenyl)-2-tert. butylamino-ethanol hydrochloride, M.p.: 235°–236° C.

(e) 1-(4'-Ethoxycarbonylamino-3'-cyano-5'-fluoro-phenyl)-2-tert. butylamino-ethanol hydrochloride, M.p.: 198°–200° C. (decomp.)

(f) 1-(4'-Ethoxycarbonylamino-3'-nitro-phenyl)-2-tert. butylamino-ethanol hydrochloride, M.p.: 189°–190° C. (decomp.)

(g) 1-(4'-Ethoxycarbonylamino-3'-fluoro-5'-iodo-phenyl)-2-cyclopropylamino-ethanol, M.p.: 127°–130° C.

(h) 1-[3'-Fluoro-5'-iodo-4'-(3-methyl-ureido)-phenyl]-2-tert. butylamino-ethanol hydrochloride, M.p.: sintering from 115° C. (amorphous substance) Mass-spectrum ($C_{14}H_{17}N_3O_2FI$): Molpeak of the base: Found: 409 Calc.: 409.25

(i) 1-[3'-Fluoro-5'-iodo-4'-(3-methyl-ureido)-phenyl]-2-cyclopropylamino-ethanol hydrochloride, M.p.: 167°–170° C.

(j) 1-(3'-Cyano-5'-fluoro-4'-isobutyloxycarbonylaminophenyl)-2-tert.-butylamino-ethanol hydrochloride, M.p.: 189°–191° C.

(k) 1-(4'-Benzyloxycarbonylamino-3'-fluoro-5'-iodophenyl)-2-cyclopropylamino-ethanol, M.p.: 135°–137° C.

(l) 1-(3'-Fluoro-4'-isobutyloxycarbonylamino-5'-iodophenyl)-2-cyclopropylamino-ethanol, M.p. 126°–128° C.

(m) 1-(4'-Ethoxycarbonylamino-3'-cyano-phenyl)-2-isopropylamino-ethanol, M.p.: 112°–115° C.

(n) 1-(4'-Ethoxycarbonylamino-3'-cyano-phenyl)-2-tert. butylamino-ethanol, M.p.: 78°–82° C.

(o) 1-[3'-Cyano-4'-(3-tert. butyl-ureido)-phenyl]-2-tert. butylamino-ethanol, M.p.: 105°–110° C. (decomp.) Mass-spectrum ($C_{18}H_{28}N_4O_2$): Molpeak of the base: Found 332 Calcul.: 332,45

The starting compound, 4'-(3-tert. butyl-ureido)-2-bromo-3'-cyano-acetophenone was prepared by reacting 4'-phenoxycarbonylamino-2-bromo-3'-cyanoacetophenone with tert. butylamine at room temperature.

The compounds of the present invention, that is, those embraced by formula I and their non-toxic, pharmacologically acceptable acid addition salts, have useful pharmacodynamic properties. More particularly, they exhibit analgesic, utero-spasmolytic, smooth-muscle antispastic, $\beta_2$-mimetic (bronchospasmolytic) and/or $\beta_1$-blocking activities in warm-blooded animals, such as guinea pigs. Moreover, they are characterized by good oral absorption and therefore produce a rapid onset of action when orally administered.

The bronchospasmolytic and antiasthmatic properties and the toxicity of the compounds of this invention were ascertained by the standard test methods described below, and the tables show the results of these tests for a few representative species of the genus, where A = 1-(4'-ethoxycarbonylamino-3'-chloro-5'-fluoro-phenyl)-2-tert.-butylamino-ethanol hydrochloride,
B = 1-(4'-ethoxycarbonylamino-3'-cyano-5'-fluoro-phenyl)-2-tert.-butylamino-ethanol hydrochloride,
C = 1-(4'-ethoxycarbonylamino-3'-cyano-phenyl)-2-tert. butylamino-ethanol hydrochloride, and
D = 1-(4'-ethoxycarbonylamino-3'-cyano-phenyl)-2-isopropylamino-ethanol hydrochloride Bronchospasmolytic activity The compounds were tested on adult guinea pigs of both sexes by the standard pharmacological test method of Konzett et al., Naunyn-Schmiedeberg's Arch. Exp. Path. Pharmakol. 195, 71–74 (1940). The test animals were anesthetized with 1.5 gm/kg urethane i.p. The bronchospasms were induced by injection of 20 mgm/kg of acetylcholine i.v. The test compound was administered intravenously or intraduodenally. From the average values of maximum decrease in bronchoconstriction obtained at various dosage levels, an $ED_{50}$ i.e. the dose which produces a 50% reduction of the bronchospasm, with confidence limits according to Fieller, Quart. J. Pharm. Phamacol. 17, 117–123 (1944), was calculated by linear regression analysis according to Linder, Statistische Methoden, 4th Ed., 148–162, published by Birkhäuser, Basel, Switzerland (1964).

The following table shows the results obtained.

TABLE I

| Compound | after i.v. administration | | after i.d. administration |
| | $ED_{50}\gamma$ /kg | t/2 min | $ED_{50}\gamma$ /kg |
|---|---|---|---|
| A | 30.7 | 60 | 32.3 |
| B | 5.6 | 70 | 7.0 |
| C | 23.5 | >50 | 8.7 |
| D | 64.0 | >50 | |

Antiasthmatic activity

The standard test method of Kallos et al., Acta med. scand. 91, 292 (1937) was used. The test compound was orally administered to adult guinea pigs which were then exposed to an acetylcholine aerosol steam produced with an aerosol nozzle at 1.5 atmospheres gauge from a 0.4% solution of acetylcholine in an aqueous 0.9% sodium chloride solution. A more than three-fold prolongation of the time until onset of the asthma attack in comparision to untreated controls was evaluated as absolute protection. From the number of animals which were protected at various dosages, an $ED_{50}$, i.e. the dose which gives absolute protection in 50% of the animals, was calculated by the method of Litchfield and Wilcoxon, J. Pahrmacol. Exper. Ther. 96, 99 (1949).

The following table shows the results obtained:

TABLE II

| Compound | $ED_{50}\gamma$ /kg p.o. | Max. effect after min. | t/2 min. |
|---|---|---|---|
| B | 14.3 | 15–30 | 150 |

Acute toxicity

The intravenous toxicity was determined on laboratory mice of both sexes having an average body weight of 20 gm. From the number of animals which died within 14 days at various dosage levels, the median lethal dose ($LD_{50}$) was calculated by the method of Litchfield and Wilcoxon, supra.

The following table shows the results obtained:

TABLE III

| Compound | $LD_{50}$ mgm/kg i.v. |
|---|---|
| A | 70.2 |
| B | 97.5 |
| C | 67.2 |
| D | 61.9 |

Thus, the compounds of the instant invention are useful for tocolysis, for the treatment of hypertension by peripheral vasodilation, for mobilization of body fat, for the treatment of allergic conditions such as allergic asthma or allergic inflammations, for the treatment of spastic disorders of the respiratory tract, and for the treatment of cardiac arrythmia.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredients such as tablets, coated pills, capsules, sprays, solutions, suspensions, emulsions, syrups, suppositories and the like. One effective dosage unit of the compounds according to the present invention is from 0.083 to 1.67 $\gamma$/kg body weight two to four times daily.

The following examples illustrate a few pharmaceutical dosage unit compositions comprising a compounds of the present invention as an active ingredient and represent the bese modes contemplated of putting the invention into practical use. The parts are parts by weight unless otherwise specified.

EXAMPLE 3

Tablets

The tablet composition is compounded from the following ingredients:

| | |
|---|---|
| 1-(4'-Ethoxycarbonylamino-3'-cyano-5'-fluoro-phenyl)-2-tert. butylamino-ethanol hydrochloride | 0.01 parts |
| Lactose | 82.49 parts |
| Potato starch | 33.00 parts |
| Polyvinylpyrrolidone | 4.00 parts |
| Magnesium stearate | 0.50 parts |
| Total | 120.00 parts |

Preparation

The active ingredient and the polyvinylpyrrolidone are dissolved in ethanol, and the resulting solution is used to uniformly moisten a homogeneous mixture of the lactose and the potato starch. The moist mass is granulated through a 1.5 mm-mesh screen, the granulate is dried at 50° C. and again passed through a 1.0 mm-mesh screen, the resulting dry granulate is admixed with the magnesium stearate, and the composition is compressed into 120 mgm-tablets in a conventional tablet making machine. Each tablet contains 10γ of the active ingredient and is an oral dosage unit composition.

EXAMPLE 4

Coated pills

The pill core composition is compounded from the following ingredients:

| | |
|---|---|
| 1-(4'-Ethoxycarbonylamino-3'-cyano-5'-fluorophenyl)-2-tert. butylamino-ethanol hydrochloride | 0.005 parts |
| Lactose | 82.495 parts |
| Potato starch | 33.000 parts |
| Polyvinylpyrrolidone | 4.000 parts |
| Magnesium stearate | 0.500 parts |
| Total | 120.000 parts |

Preparation

The pill core composition is compounded in the same manner as the tablet composition in Example 3, and the composition is compressed into 120 mgm-pill cores which are subsequently coated with a thin shell consisting essentially of sugar and talcum and finally polished with beeswax. Each coated pill contains 5γ of the active ingredient and is an oral dosage unit composition.

EXAMPLE 5

Gelatin capsules

The capsule filler composition is compounded from the following ingredients:

| | |
|---|---|
| 1-(4'-Ethoxycarbonylamino-3'-cyano-5'-fluoro phenyl)-2-tert. butylamino-ethanol hydrochloride | 0.01 parts |
| Lactose | 59.99 parts |
| Corn starch | 60.00 parts |
| Total | 120.00 parts |

Preparation

The active ingredient, the lactose and the corn starch are intimately admixed with each other, and 120 mgm-portions of the mixture are filled into gelatin capsules of suitable size. Each capsule contains 10γ of the active ingredient and is an oral dosage unit composition.

EXAMPLE 5

Hypodermic solution

The solution is compounded from the following ingredients:

| | |
|---|---|
| 1-(4'-Ethoxycarbonylamino-3'-cyano-5'-fluorophenyl)-2-tert. butylamino-ethanol hydrochloride | 0.01 parts |
| Citric acid | 2.5 parts |
| Sodium acid phosphate | 7.5 parts |
| Sodium chloride | 4.6 parts |
| Double-distilled water    q.s.ad | 2000 parts by vol. |

Preparation

The active ingredient, the buffers and the sodium chloride are dissolved in the distilled water, the solution is filtered until free from suspended matter, and the filtrate is filled, in a inert atmosphere of nitrogen, into 2 cc-brown ampules which are then sealed and sterilized for 20 minutes at 120° C. Each ampule contains 10γ of the active ingredient, and the contents thereof are an injectable dosage-unit composition.

EXAMPLE 7

Rectal Suppositories

The suppository composition is compounded from the following ingredients:

| | |
|---|---|
| 1-(4'-Ethoxycarbonylamino-3'-cyano-5'-fluorophenyl)-2-tert. butylamino-ethanol | 0.01 parts |
| Suppository base (e.g. cocoa butter) | 1699.99 parts |
| Total | 1700.00 parts |

Preparation

The finely pulverized active ingredient is stirred, with the aid of an immersion homogenizer, into the suppository base which had previously been melted and cooled to 40° C. 1.7 gm-portions of the mixture are poured at 37° C. into cooled suppository molds and allowed to harden therein. Each suppository contains 10γ of the active ingredient and is a rectal dosage unit composition.

EXAMPLE 8

Syrup

The syrup is compounded from the following ingredients:

| | |
|---|---|
| 1-(4'-Ethoxycarbonylamino-3'-cyano-5'-fluorophenyl)-2-tert. butylamino-ethanol hydrochloride | 0.0001 parts |
| Benzoic acid | 0.1 parts |
| Tartaric acid | 1.0 parts |
| Sugar | 50.0 parts |
| Flavoring | 1.0 parts |
| Food color | 0.05 parts |
| Distilled water | 100.0 parts |

Preparation

About 60 parts of distilled water are heated to 80° C., the benzoic acid, the tartaric acid, the active ingredient, the food color and the sugar are successively dissolved therein, the solution is allowed to cool to room temperature, the flavoring is added, the remaining amount of distilled water added, and the resulting syrup is filtered. Each 10 ml of the syrups contain 10γ of the active ingredient and are an oral dosage unit composition.

Any one of the other compounds embraced by formula I or a non-toxic acid addition salt thereof may be substituted for the particular active ingredient in Examples 3 through 8. Likewise, the amount of active ingredient in these illustrative examples may be varied to achieve the dosage unit range set forth above, and the amounts and nature of the inert pharmaceutical carrier ingredients may be varied to meet particulare requirements.

While the present invention has been illustrated with the aid of certain specific embodiments thereof, it will be readily apparent to others skilled in the art that the invention is not limited to these particular embodiments, and that various changes and modification may be made without departing from the spirit of the invention or the scope of the appended claims.

We claim:
1. A compound of the formula

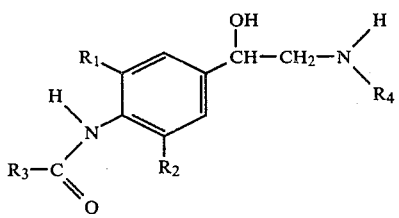

wherein
$R_1$ is hydrogen, halogen or cyano;
$R_2$ is fluorine, cyano, trifluoromethyl, nitro or alkyl of 1 to 4 carbon atoms;
$R_3$ is alkoxy of 1 to 5 carbon atoms, alkenyloxy of 2 to 5 carbon atoms, aryloxy of 6 to 10 carbon atoms, aralkoxy of 7 to 11 carbon atoms, or
—$NR_5R_6$, where $R_5$ and $R_6$ are each hydrogen, alkyl of 1 to 5 carbon atoms, alkenyl of 2 to 5 carbon atoms, aryl of 6 to 10 carbon atoms or aralkyl of 7 to 11 carbon atoms; and
$R_4$ is cycloalkyl of 3 to 5 carbon atoms or alkyl of 3 to 5 carbon atoms;
or a non-toxic, pharmacologically acceptable acid addition salt thereof.

2. A compound of claim 1,
where
$R_1$ is hydrogen, halogen or cyano;
$R_2$ is fluorine, cyano, trifluoromethyl, nitro or alkyl of 1 to 4 carbon atoms;
$R_3$ is alkoxy of 1 to 5 carbon atoms, alkenyloxy of 2 to 5 carbon atoms, aralkoxy of 7 to 11 carbon atoms or, when $R_1$ is hydrogen or halogen and $R_2$ is fluorine, trifluoromethyl or nitro, also
—$NHR_6$, where $R_6$ is hydrogen, alkyl of 1 to 5 carbon atoms, alkenyl of 2 to 5 carbon atoms, aryl of 6 to 10 carbon atoms or aralkyl of 7 to 11 carbon atoms; and
$R_4$ is cycloalkyl of 3 to 5 carbon atoms or alkyl of 3 to 5 carbon atoms;
or a non-toxic, pharmacologically acceptable acid addition salt thereof.

3. A compound of claim 1,
where
$R_1$ is hydrogen, halogen or cyano;
$R_2$ is fluorine, cyano, trifluoromethyl, nitro or alkyl of 1 to 4 carbon atoms;
$R_3$ is alkoxy of 1 to 4 carbon atoms or, when $R_1$ is hydrogen or halogen and $R_2$ is fluorine, trifluoromethyl or nitro, also —$HNR_6$ where $R_6$ is hydrogen or alkyl of 1 to 4 carbon atoms; and
$R_4$ is isopropyl or tert. butyl;
or a non-toxic, pharmacologically acceptable acid addition salt thereof.

4. A compound of claim 1,
where
$R_1$ is hydrogen, halogen or cyano;
$R_2$ is fluorine, cyano, trifluoromethyl or nitro;
$R_3$ is alkoxy of 1 to 4 carbon atoms; and
$R_4$ is isopropyl or tert. butyl;
or a non-toxic, pharmacologically acceptable acid addition salt thereof.

5. A compound according to claim 1 having bronchospasmolytic activity selected from the group consisting of: 1-(4'-ethoxycarbonylamino-3'-cyano-5'-fluoro-phenyl)-2-tert.butylamino ethanol;
1-(4'-ethoxycarbonylamino-3'-cyano-phenyl)-2-tert.butyl-amino-ethanol;
1-(4'-ethoxycarbonylamino-3'-cyano-phenyl)-2-isopropylamino-ethanol
and their non-toxic, pharmacologically acceptable acid addition salts.

6. A compound of claim 1 having bronchospasmolytic activity selected from the group consisting of:
1-(4'-ethoxycarbonylamino-3'-chloro-5'-fluoro-phenyl)-2-tert.butylamino ethanol;
1-(4'-ethoxycarbonylamino-3'-cyano-5'-fluoro-phenyl)-2-tert.butylamino ethanol;
1-(4'-ethoxycarbonylamino-3'-cyano-phenyl)-2-tert.butylamino-ethanol;
1-(4'-ethoxycarbonylamino-3'-3'-cyano-phenyl)-2-isopropylamino-ethanol
and their non-toxic, pharmacologically acceptable addition salts.

7. A compound of claim 6, which is 1-(4'-ethoxycarbonyllamino-3'-chloro-5'-fluoro-phenyl)-2-tert.-butylaminoethanol or a non-toxic, pharmacologically acceptable acid addition salt thereof.

8. A compound of claim 6, which is 1-(4'-ethoxycarbonylamino-3'-cyano-5'-fluoro-phenyl)-2-tert.-butylamino-ethanol or a non-toxic, pharmacologically acceptable acid addition salt thereof.

9. A compound of claim 6, which is 1-(4'-ethoxycarbonylamino-3'-cyano-phenyl)-2-tert. butylamino-ethanol or a non-toxic, pharmacologically acceptable acid addition salt thereof.

10. A compound of claim 6, which is 1-(4'-ethoxycarbonylamino-3'-cyano-phenyl)-2-isopropylamino-ethanol or a non-toxic, pharmacologically acceptable acid addition salt thereof.

11. A bronchospasmolytic pharmaceutical dosage unit composition consisting essentially of an inert pharmaceutical carrier and an effective bronchospasmolytic amount of a compound of claim 6.

12. The method of antagonizing bronchospasm in a warm-blooded animal in need thereof, which comprises perorally, parenterally or rectally administering to said animal an effective bronchospasmolytic amount of a compound of claim 6.

* * * * *

UNITED STATES PATENT AND TRADEMARK OFFICE
CERTIFICATE OF CORRECTION

PATENT NO. : 4,214,001
DATED : July 22, 1980
INVENTOR(S) : GÜNTHER ENGELHARDT ET AL.

It is certified that error appears in the above-identified patent and that said Letters Patent are hereby corrected as shown below:

Column 11, line 39: "-$NHR_6$" should read -- -$HNR_6$ --.

Column 12, line 29: Cancel "3'-", second occurrence.

Column 12, lines 33/34: "ethoxy-carbonyllamino" should read -- ethoxy-carbonylamino --.

Signed and Sealed this

Second Day of December 1980

[SEAL]

Attest:

SIDNEY A. DIAMOND

Attesting Officer

Commissioner of Patents and Trademarks